United States Patent
Mochel et al.

(10) Patent No.: US 10,111,848 B2
(45) Date of Patent: *Oct. 30, 2018

(54) TRIHEPTANOIN FOR THE TREATMENT OF GLUCOSE TRANSPORT 1 DEFICIENCY

(71) Applicants: National Institute of Health and Medical Research, Paris (FR); Baylor Research Institute, Dallas, TX (US)

(72) Inventors: Fanny Mochel, Paris (FR); Raphael Schiffmann, Rockwall, TX (US)

(73) Assignees: National Institute of Health and Medical Research, Paris (FR); Baylor Research Institute, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/257,363

(22) Filed: Sep. 6, 2016

(65) Prior Publication Data

US 2016/0374980 A1   Dec. 29, 2016

Related U.S. Application Data

(63) Continuation of application No. 14/106,078, filed on Dec. 13, 2013, now Pat. No. 9,468,229.

(60) Provisional application No. 61/779,942, filed on Mar. 13, 2013, provisional application No. 61/737,013, filed on Dec. 13, 2012.

(51) Int. Cl.
| | |
|---|---|
| *A61K 31/225* | (2006.01) |
| *A01N 37/06* | (2006.01) |
| *A01N 37/02* | (2006.01) |
| *A61K 31/23* | (2006.01) |
| *A61K 45/06* | (2006.01) |
| *A23L 33/12* | (2016.01) |
| *A61B 6/03* | (2006.01) |
| *A61B 6/00* | (2006.01) |
| *A61K 9/00* | (2006.01) |
| *A61K 9/48* | (2006.01) |
| *G01N 33/64* | (2006.01) |

(52) U.S. Cl.
CPC ............ *A61K 31/225* (2013.01); *A23L 33/12* (2016.08); *A61B 6/037* (2013.01); *A61B 6/501* (2013.01); *A61K 9/0053* (2013.01); *A61K 9/48* (2013.01); *A61K 31/23* (2013.01); *A61K 45/06* (2013.01); *G01N 33/64* (2013.01); *A23V 2002/00* (2013.01)

(58) Field of Classification Search
CPC ...... A61K 31/23; A61K 31/225; A61K 45/06; A61K 9/0053; A61K 9/48; A23L 33/12; A23V 2002/00; A61B 6/037; A61B 6/501; G01N 33/64
USPC ........................................................ 514/547
See application file for complete search history.

(56) References Cited

U.S. PATENT DOCUMENTS

| | | | |
|---|---|---|---|
| 4,025,649 | A | 5/1977 | Taillandier et al. |
| 4,753,963 | A | 6/1988 | Jandacek |
| 6,335,361 | B1 | 1/2002 | Hamilton |
| 6,740,679 | B1 | 5/2004 | Roe |
| 6,835,750 | B1 | 12/2004 | Henderson |
| 8,399,515 | B2 | 3/2013 | Roe |
| 9,468,229 | B2 | 10/2016 | Mochel et al. |
| 9,717,705 | B2 | 8/2017 | Duff et al. |
| 9,833,430 | B2 | 12/2017 | Borges et al. |
| 2006/0004099 | A1 | 1/2006 | Roe |
| 2006/0189545 | A1 | 8/2006 | Henderson et al. |
| 2007/0123588 | A1 | 5/2007 | Charles |
| 2008/0085920 | A1 | 4/2008 | Donello et al. |
| 2008/0132571 | A1 | 6/2008 | Roe |
| 2008/0287372 | A1 | 11/2008 | Henderson |
| 2009/0253781 | A1 | 10/2009 | Veech |
| 2010/0063147 | A1 | 3/2010 | Durr et al. |
| 2011/0201558 | A1 | 8/2011 | Roe et al. |
| 2011/0301238 | A1 | 12/2011 | Borges |
| 2011/0301328 | A1 | 12/2011 | Borges |
| 2011/0306663 | A1 | 12/2011 | Schiffmann et al. |
| 2012/0164243 | A1 | 6/2012 | Rinsch et al. |
| 2012/0165405 | A1 | 6/2012 | Durr et al. |
| 2012/0329829 | A1 | 12/2012 | Hauske |
| 2013/0123359 | A1 | 5/2013 | Roe |
| 2014/0221482 | A1 | 8/2014 | Mochel et al. |
| 2014/0364498 | A1 | 12/2014 | Durr et al. |
| 2016/0263071 | A1 | 9/2016 | Borges et al. |
| 2016/0296491 | A1 | 10/2016 | Mochel |
| 2018/0021287 | A1 | 1/2018 | Durr et al. |

FOREIGN PATENT DOCUMENTS

| | | |
|---|---|---|
| DE | 3032300 A1 | 4/1982 |
| EP | 1929995 | 6/2008 |
| EP | 2599482 A1 | 6/2013 |
| GB | 2104079 A | 3/1983 |
| JP | H6-287138 | 10/1994 |
| KR | 10-2001-0108173 | 12/2001 |
| WO | WO 2000/045649 | 8/2000 |
| WO | WO 2001/082928 | 11/2001 |
| WO | WO 2004/077938 | 9/2004 |
| WO | WO 2004/103307 | 12/2004 |

(Continued)

OTHER PUBLICATIONS

Supplementary European Search Report and Written Opinion for European Application No. 10841613.2, dated Jun. 4, 2013, 10 pages.
International Search Report and Written Opinion for International Application No. PCT/US2010/062054, dated Feb. 23, 2011, 9 pages.
Supplementary European Search Report and Written Opinion for European Application No. 13862044.8, dated Jun. 29, 2016, 7 pages.
International Search Report and Written Opinion for International Patent Application No. PCT/US2014/065670, dated Feb. 12, 2015, 11 pages.

(Continued)

*Primary Examiner* — My-Chau T. Tran
(74) *Attorney, Agent, or Firm* — Cooley LLP

(57) ABSTRACT

Provided are methods for treating GLUT1 and related brain energy deficiencies comprising administering odd-carbon fatty acid sources, e.g., C5 or C7 fatty acid sources, and related compositions.

8 Claims, No Drawings

(56) References Cited

FOREIGN PATENT DOCUMENTS

| WO | WO 2008/068230 | 6/2008 |
| --- | --- | --- |
| WO | WO 2009/018478 A2 | 2/2009 |
| WO | WO 2009/124250 | 10/2009 |
| WO | WO 2011/082111 | 7/2011 |
| WO | WO 2011/159634 | 12/2011 |
| WO | WO 2014/093901 | 6/2014 |
| WO | WO 2015/073803 | 5/2015 |

OTHER PUBLICATIONS

Supplemental European Search Report for European Application No. 06291873.5, dated Jun. 12, 2007, 9 pages.
European Search Report for European Application No. 15175719.2, dated Feb. 3, 2016, 7 pages.
International Search Report and Written Opinion for International Application No. PCT/EP2007/063181, dated Apr. 21, 2008, 10 pages.
Andreassen, O. A. et al., "Dichloroacetate exerts therapeutic effects in transgenic mouse models of Huntington's disease," Annals of Neurology, 50(1):112-117 (Jul. 2001).
Antonini, A. et al., "Striatal glucose metabolism and dopamine D2 receptor binding in asymptomatic gene carriers and patients with Huntington's disease," Brain, 119(Pt 6):2085-2095 (1996).
Aso, E. et al., "Triheptanoin supplementation to ketogenic diet curbs cognitive impairment in APP/PS1 mice used as a model of familial alzheimer's disease," Current Alzheimer Research, 10(3):290-297 (2013).
Beal, M. F., "Energetics in the pathogenesis of neurodegenerative diseases," Trends in Neurosciences, 23(7):298-304 (Jul. 2000).
Beal, M. F. et al., "Neurochemical and histologic characterization of striatal excitotoxic lesions produced by the mitochondrial toxin 3-nitropropionic acid," J. Neurosci., 13(10):4181-4192 (1993).
Borges, K. et al. "Gene expression changes after seizure preconditioning in the three major hippocampal cell layers," Neurobiology of Disease, 26:66-77 (Jan. 2007).
Borges, K. et al., "Anti-Epileptic Effects of Triheptanoin in Two Chronic Mouse Epilepsy Models," presented at the 24th Annual Scientific Meeting, Epilepsy Society of Australia, Perth Convention Exhibition Center (Nov. 2-4, 2009).
Breen, C., "Unsuccessful treatment of severe pyruvate carboxylase deficiency with triheptanoin," Eur. J. Pediatr., 173:361-366 (2014).
Buckner, R. L. et al., "The Brain's Default Network, Anatomy, Function, and Relevance to Disease," Ann. N.Y. Acad. Sci., 1124:1-38 (2008).
Clarke, D. D. et al., "Circulation and energy metabolism of the brain," Chapter 31 in: Siegel G. J. et al. (eds.), Basic Neurochemistry: Molecular, Cellular and Medical Aspects, 6th edition, Philadelphia: Lippincott-Raven, 638-669 (1999).
de Bandt, J-P. et al., "Therapeutic use of branched-chain amino acids in burn, trauma, and sepsis," J. Nutr., 136(1 Suppl):308S-313S (2006).
Deng, S. et al., "Interrelations between C4 Ketogenesis, C5 Ketogenesis, and anaplerosis in the perfused rat liver," The Journal of Biological Chemistry, 284(41):27799-27807 (Oct. 2009).
Ferrante, R. J. et al., "Neuroprotective effects of creatine in a transgenic mouse model of Huntington's disease," J. Neurosci., 20(12):4389-4397 (2000).
Gabuzda, D. et al., "Inhibition of energy metabolism alters the processing of amyloid precursor protein and induces a potentially amyloidogenic derivative," The Journal of Biological Chemistry, 269(18):13623-13628 (1994).
Glenner, G. G et al., "The amyloid deposits in Alzheimer's disease: their nature and pathogenesis," Appl. Pathol., 2(6):357-369 (1984).
Goedert, M. et al., "Cloning and sequencing of the cDNA encoding a core protein of the paired helical filament of Alzheimer disease: Identification as the microtubule-associated protein tau," Proc. Natl. Acad. Sci. USA, 85(11):4051-4055 (1988).
Grundke-Iqbal, I. et al., "Abnormal Phosphorylation of the Microtubule-Associated Protein (tau) in Alzheimer Cytoskeletal Pathology," Proc. Natl. Acad, Sci., 83(13):4913-4917 (1986).
Guy, D. G. et al., "Effect of diets high in carbohydrate, soy oil, medium-chain triglycerides or tripelargonin on blood and liver lipid and glucose intermediates in meal-eating rats," J. Nutr., 111:1437-1445 (1981).
Hardy, J. A. et al., "Alzheimer's disease: the amyloid cascade hypothesis," Science, 256(5054):184-185 (Apr. 1992).
Henderson, S. T., "Ketone bodies as a therapeutic for Alzheimer's disease," Neurotherapeutics, 5(3):470-480 (Jul. 2008).
Henderson, S. T. et al., "Study of the ketogenic agent AC-1202 in mild to moderate Alzheimer's disease: a randomized, double-blind, placebo-controlled, multicenter trial," Nutrition & Metabolism, 6:31 (Aug. 2009) Available online; <URL: http://www.nutritionandmetabolism.com/content/6/1/31>, 25 pages.
Kashiwaya, Y. et al., "D-β-Hydroxybutyrate protects neurons in models of Alzheimer's and Parkinson's disease," PNAS, 97(10):5440-5444 (May 2000).
Kinman, R. P. et al., "Parenteral and enteral metabolism of anaplerotic triheptanoin in normal rats," Am. J. Physiol. Endocrinol Metab., 291(4):E860-E866 (2006).
Loscher, W., "Critical review of current animal models of seizures and epilepsy used in the discovery and development of new antiepileptic drugs," Seizure, 20:359-368 (2011).
Masters, C. L. et al., "Amyloid Plaque Core Protein in Alzheimer Disease and Down Syndrome," Proc. Natl. Acad. Sci., 82(12):4245-4249 (Jun. 1985).
Milakovic, T. et al., "Mitochondrial respiration and ATP production are significantly impaired in striatal cells expressing mutant huntingtin," J. Biol. Chem., 280(35):30773-30782 (2005).
Mochel, F. et al., "Early energy deficit in Huntington disease: identification of a plasma biomarker traceable during disease progression," Plos One, 2(7):e647 (2007). doi:10.1371/journal.prone.0000647.
Neal, E. G. et al., "A randomized trial of classical and medium-chain triglyceride ketogenic diets in the treatment of childhood epilepsy," Epilepsia, 50(5):1109-1117 (May 2009).
Pascual, J. M. et al., "Brain glucose supply and the syndrome of infantile neuroglycopenia," Archives of Neurology, 64(4):507-513 (Apr. 2007).
Rangone, H. et al., "Phosphorylation of arfaptin 2 at Ser260 by Akt Inhibits PolyQ-huntingtin-induced toxicity by rescuing proteasome impairment," J. Biol. Chem., 280(23):22021-22028 (2005).
Reger, M. A. et al., "Effects of β-hydrozybutyrate on cognition in memory-impaired adults," Neurobiology of Aging, 25(3):311-314 (2004).
Reszko, A. E. et al., "Assessing the reversibility of the anaplerotic reactions of the propionyi-CoA pathway in heart and liver," J. Biol. Chem., 278(37):34959-34965 (2003).
Sabatine, M. S. et al., "Metabolomic identification of novel biomarkers of myocardial ischemia," Circulation, 112(25):3868-3875 (2005).
Segal, K. R. et al., "Lean body mass estimation by bioelectrical impedance analysis: a four-site cross-validation study," Am. J. Clin. Nutr., 47(1):7-14 (1988).
Seyfried, T. N. et al., "Ketone strong: Emerging evidence for a therapeutic role of ketone bodies in neurological and neurodegenerative diseases," Journal of Lipid Research, 55:1815-1817 (2014).
Stafstrom, C. E. et al., "The ketogenic diet as a treatment paradigm for diverse neurological disorders," Frontiers in Pharmacology, vol. 3, Article 59, pp. 1-8 (Apr. 2012).
Stepan Company, NEOBEE 895, Overview (2012), 3 pages (online), Retrieved from the Internet: <URL: http://www.stepan.com/Products/Specialty-Products/NEOBEE/NEO . . . >, Retrieved on: Jan. 21, 2015.
Thomas, N. K. et al., "Triheptanoin in acute mouse seizure models," Epilepsy Research, 99:312-317 (2012).
Underwood, B. R. et al., "Huntington disease patients and transgenic mice have similar pro-catabolic serum metabolite profiles," Brain, 129:877-886 (2006).
Van Der Auwera, I. et al., "A ketogenic diet reduces amyloid beta 40 and 42 in a mouse model of Alzheimer's disease," Nutrition & Metabolism, 2:28 (2005).

(56) References Cited

OTHER PUBLICATIONS

Veech, R. L. et al., "Ketone bodies, potential therapeutic uses," IUBMB Life, 51:241-247 (2001).
Velliquette, R. A., et al., "Energy inhibition elevates β-secretase levels and activity and is potentially amyloidogenic in APP transgenic mice: Possible early events in Alzheimer's disease pathogenesis," The Journal of Neuroscience, 25(47):10874-10883 (2005).
Vlaeminck, B. et al., "Milk odd- and branched-chain fatty acids in relation to the rumen fermentation pattern," Journal of Dairy Science, 89(10):3954-3964 (Oct. 2006).
Walsh, M. C. et al., "Effect of acute dietary standardization on the urinary, plasma, and salivary metabolomic profiles of healthy humans[1-3]," Am. J. Clin. Nutr., 84(3):531-539 (2006).
Wang, X. et al., "Anaplerosis from heptanoate—a propionyl-CoA precursor—in mouse brain," The FASEB Journal, 21:541.12 (2007) (Abstract).
White, H. S., "Preclinical Development of Antiepileptic Drugs: Past, Present, and Future Directions," Epilepsia, 44(7):2-8 (2003).
Wikipedia, Definition of "Axona," [Retrieved on Feb. 9, 2013], Retrieved from the Internet: <URL: http://en.wikipedia/org/wiki/Axona>, 3 pages.
Wikipedia, Definition of "Fatty Acid," [Retrieved on Oct. 13, 2016], Retrieved from the Internet: <URL: https://en.wikipedia/org/wiki/Fatty_Acid>, 7 pages.
Willis, S. et al., "The effect of anaplerotic diet in mouse epilepsy models," Presentation Abstract, Program#/Poster #: 539.8/P4, Neuroscience Meeting Planner, Chicago, IL: Society for Neuroscience, 2009.
Zhao, W. et al., "Caprylic triglyceride as a novel therapeutic approach to effectively improve the performance and attenuate the symptoms due to the motor neuron loss in ALS disease," PloS ONE 7(11):e49191 (2012). doi:10.1371/journal.pone.0049191.
Bjorkqvist, M. et al., "The R6/2 transgenic mouse model of Huntington's disease develops diabetes due to deficient b-cell mass and exocytosis," Human Molecular Genetics, 2005, 14(5):565-574, doi:10.1093/hmg/ddi053, Advance Access published on Jan. 13, 2005.
Boesgaard, T. W. et al., "Huntington's Disease does not appear to increase the risk of diabetes mellitus," Journal of Neuroendocrinology, vol. 21, Issue 9, Sep. 2009, pp. 770-776.
Farrer, L. A., "Diabetes mellitus in Huntington disease," Clinical Genetics 1985, 27:62-67.
Hurlbert, M. S. et al., "Mice transgenic for an expanded CAG repeat in the Huntington's Disease gene develop diabetes," Diabetes Mar. 1999; 48(3): 649-651. https://doi.org/10.2337/diabetes.48.3.649.
IP High Court Case No. Heisei 21 (Gyoke) 10033, decided on Jan. 28, 2010, Brief History of the case, pp. 14-17.
Lalic, N. M. et al., "Glucose homeostasis in Huntington Disease. Abnormalities in insulin sensitivity and early-phase insulin secretion," Arch Neurol. 2008;65(4):476-480.
McDonald, T. S. et al., "Alterations of hippocampal glucose metabolism by even versus uneven medium chain triglycerides," Journal of Cerebral Blood Flow & Metabolism (2014) 34, 153-160.
Mosconi, L. et al., "Brain Glucose Hypometabolism and Oxidative Stress in Preclinical Alzheimer's Disease," Ann N Y Acad Sci. Dec. 2008; 1147:180-195. doi:10.1196/annals.1427.007.
Podolsky, S. et al., "Increased frequency of diabetes mellitus in patients with Huntington's chorea," The Lancet, vol. 299, Issue 7765, Jun. 24, 1972, pp. 1356-1359. Originally published as vol. 1, Issue 7765.
Pong et al., "Glucose transporter type I deficiency syndrome: Epilepsy phenotypes and outcomes" *Epilepsia*, 53(9):1503-1510, 2012.
Borges, K., Sonnewald, U., "Triheptanoin—A medium chain triglyceride with odd chain fatty acids: A new anaplerotic anticonvulsant treatment?", *Epilepsy Res.* (2011), doi:10.1016/j.eplepsyres.2011.05.023.
Kudin, A.P. et al., "Mitochondrial involvement in temporal lobe epilepsy", *Experimental Neurology*, 218:326-332 (2009).
Marin-Valencia, I. et al., "Heptanoate as a neural fuel: energetic and neurotransmitter precursors in normal and glucose transporter I-deficient (G1D) brain", *Journal of Cerebral Blood Flow & Metabolism* (2012) doi:10.1038/jcbfm.2012.151.
Pascual, Juan, Dr., GLUT1 Transporter Deficiency Syndrome Conference, Cinical Research, Louisville, Kentucky, Jul. 25, 2010, 21 pages.
Willis, S. et al., "Anticonvulsant effects of a triheptanoin diet in two mouse chronic seizure models", *Neurobiology of Disease*, 40:565-572 (2010).
Borges, Slides Presented at the International Symposium on Dietary Therapies for Epilepsy and Other Neurological Disorders in Phoenix, Arizona on Mar. 8, 2008.
Borges, Slides Printed and Distributed at the International Symposium on Dietary Therapies for Epilepsy and Other Neurological Disorders in Phoenix, Arizona on Mar. 8, 2008.
Marcela, M. et al., "Effects of short-term and long-term treatment with medium- and long-chain triglycerides ketogenic diet on cortical spreading depression in young rats", *Neuroscience Letters*, 434:66-70 (2008).
Perlman, B.J. et al., "Membrane-Disordering Potency and Anticonvulsant Action of Valproic Acid and Other Short-Chain Fatty Acids", *Molecular Pharmacology*, 26:83-89 (1984).
Brockmann, K., "The expanding phenotype of GLUT1-deficiency syndrome," Brain Development, 2009, 31:545-552.
Brunengraber, H. et al., "Anaplerotic molecules: current and future," J Inherit Metab Dis., 2006, 29:327-331.
Freeman, J. M. et al., "Ketosis and the ketogenic diet, 2010: advances in treating epilepsy and other disorders," Adv. Pediatr., 2010, 57:315-329.
Graham, J. M. Jr., "GLUT1 deficiency syndrome as a cause of encephalopathy that includes cognitive disability, treatment-resistant infantile epilepsy and a complex movement disorder," Eur J Med Genet., 2012, 55(5):232-234.
Klepper, J. et al., "GLUT1 deficiency syndrome—2007 update," Dev Med Child Neurol., 2007, 49:707-716.
Klepper, J., "GLUT1 deficiency syndrome in clinical practice," Epilepsy Research, 100(3):272-277 (2012).
Mochel, F. et al., "Dietary anaplerotic therapy improves peripheral tissue energy metabolism in patients with Huntington's disease," Eur J Hum Genet., 2010, 18:1057-1060.
Mochel, F. et al., "Pyruvate carboxylase deficiency: clinical and biochemical response to anaplerotic diet therapy," Mol Genet Metab., 2005, 84:305-312.
Roe, C. R. et al., "Anaplerotic diet therapy in inherited metabolic disease: therapeutic potential," J Inherit Metab Dis., 2006, 29:332-240.
Roe, C. R. et al., "Treatment of cardiomyopathy and rhabdomyolysis in long-chain fat oxidation disorders using an anaplerotic odd-chain triglyceride," J Clin Invest., 2002, 110:259-269.
Roe, C. R. et al., "Carnitine palmitoyltransferase II deficiency: successful anaplerotic diet therapy," Neurology, 2008, 71:260-264.
Schneider, S. A. et al., "GLUT1 gene mutations cause sporadic paroxysmal exercise-induced dyskinesias," Mov Disord., 2009, 24:1684-1688.
Seidner, G. et al., "GLUT-1 deficiency syndrome caused by haploinsufficiency of the blood-brain barrier hexose carrier," Nat Genet., 1998, 18:188-191.
Striano, P. et al., "GLUT1 mutations are a rare cause of familial idiopathic generalized epilepsy," Neurology, 2012, 78:557-562.
Verrotti et al., Eur. J. Paedeatr. Neurol., 16:3-9 (2012).
Wang, D. et al., "GLUT-1 deficiency syndrome: clinical, genetic, and therapeutic aspects," Ann Neurol., 2005, 57:111-118.
International Search Report for International Application No. PCT/US2013/075146, dated Mar. 11, 2014.
Written Report for International Application No. PCT/US2013/075146, dated Mar. 11, 2014.
Leen et al. "Glucose transporter-1 deficiency syndrome: the expanding clinical and genetic spectrum of a treatable disorder", Mar. 2010. *Brain*, 133(3):655-670, Published Oline on Feb. 2, 2010.
Supplementary European Search Report for European Application No. 14861265.8, dated Jun. 1, 2017, 10 pages.
Glut1 Deficiency Foundation Newsletter, 2013 Glut1 Deficiency Family Conference, 5th Family Conference, Houston, Jul. 11-12,

(56) References Cited

OTHER PUBLICATIONS 2013, vol. 9, Spring 2013. Retrieved from the Internet: <URL: :http://www.g1dfoundation.org/wp-content/uploads/2013/05/Spring-2013-G1D-News.pdf>, 13 pages.
"Curing the Epilepsies 2013: Pathways Forward," Program Materials, Apr. 17-19, 2013, Natcher Conference Center, National Institutes of Health, Bethesda, Maryland, National Institute of Neurological Disorders and Stroke, Retrieved from the Internet: https://meetings.ninds.nih.gov/assets/2013epilepsies/CuringEpilepsies2013_PROGRAMBOOK.pdf, 204 pages.
Ingle, D. L. et al., "Dietary energy value of medium-chain triglycerides," Journal of Food Science, 64(6):960-963 (1999).
Ito, Y. et al., "Clinical presentation, EEG studies, and novel mutations in two cases of GLUT1 deficiency syndrome in Japan," Brain & Development, 27(4):311-317 (2005).
Pascual, J. M. et al., "Imaging the metabolic footprint of Glut1 deficiency on the brain," Ann. Neurol., 52(4):458-464 (Oct. 2002).
Mochel, F., U.S. Appl. No. 15/878,373, "Compositions and Methods for Treatment of Movement Disorders," filed Jan. 23, 2018, 25 pages.
Anger, W. K., "Animal test systems to study behavioral dysfunctions of neurodegenerative disorders," NeuroToxicology 12:403-413, 1991.
Sarter, M., "Animal cognition: defining the issues," Neuroscience and Biobehavioral Reviews 28 (2004) 645-650.
Tayebati, S. K., "Animal models of cognitive dysfunction," Mechanisms of Ageing and Development, 127 (2006) 100-108.
Cambridge English Dictionary, The meaning of "treat" [online], Retrieved from the Internet: <URL: https://dictionary.cambridge.org/dictionary/english/treat>, Retrieved from the Internet on Mar. 19, 2018, 3 pages.

TRIHEPTANOIN FOR THE TREATMENT OF GLUCOSE TRANSPORT 1 DEFICIENCY

CROSS-REFERENCE TO RELATED PATENT APPLICATIONS

The present application is a Continuation of U.S. patent application Ser. No. 14/106,078, filed on Dec. 13, 2013, which claims priority to and the benefit of U.S. Provisional Patent Application Ser. No. 61/779,942, filed on Mar. 13, 2013, and U.S. Provisional Patent Application Ser. No. 61/737,013, filed on Dec. 13, 2012, each of which is hereby incorporated in its entirety for all purposes.

BACKGROUND

Technical Field

Embodiments of the present invention relate to methods for treating GLUT1 and related brain energy deficiencies comprising administering odd-carbon fatty acid sources, e.g., C5 or C7 fatty acid sources, and related compositions.

Description of the Related Art

GLUT1 deficiency is a rare progressive neurogenetic disorder characterized by encephalopathy with progressive intellectual disability, drug-resistant epilepsy, motor disorders, and acquired microcephaly.[1-4] The clinical spectrum of GLUT1 deficiency syndrome includes developmental delay and movement disorders without epilepsy,[4] as well as familial and sporadic paroxysmal exercise-induced dyskinesia with or without epilepsy.[5] There are varying degrees of cognitive impairment with dysarthria, dysfluency, and expressive language deficits that are more severe than receptive language deficits. In most patients, the cerebrospinal fluid (CSF) to blood glucose ratio is below 0.50, and CSF lactate is low to normal.[3] GLUT1 deficiency can be diagnosed by mutation analysis of the SLC2A1 gene, and deficient GLUT1 function confirmed by analysis of glucose uptake into erythrocytes.

Early diagnosis of GLUT1 deficiency is critical because it allows for treatment with a ketogenic diet, a severely restricted diet consisting of 70-90% fat and very low carbohydrate diet that mimics the metabolic state of fasting. Ketogenic diets generate ketone bodies as an alternative energy source for the brain and can thereby reduce the frequency of seizures and dystonic movements.[6,7] Because ketone bodies are not affected by the GLUT1 defect (ketone bodies use another transporter to enter the central nervous system), they can supply an alternative source of fuel to the brain, effectively correcting the brain energy metabolism deficiency.[7] However, ketogenic diets are difficult to comply with long-term because of certain adverse side effects the extreme dietary choices require. Side effects of ketogenic diets include constipation, low-grade acidosis, hypoglycemia, hyperlipidemia and hypercholesterolemia. Long-term ketogenic diets may cause retarded growth, bone fractures, and kidney stones.[8]

Accordingly, there remains a need in the art for treating GLUT1 deficiencies and similar defects in brain energy metabolism.

BRIEF SUMMARY OF THE INVENTION

Embodiments of the present invention include methods of treating a GLUT1 deficiency in a subject in need thereof, comprising administering to the subject an odd-chain fatty acid source. In some embodiments, the subject has a disease-associated mutation in at least one SLC2A1 gene.

In certain embodiments, the subject has experienced one or more of seizures, developmental delay, acquired microcephaly, spasticity, ataxia, or paroxysmal exertion-induced dyskinesia.

In particular embodiments, the subject has hypoglycorrhachia without hypoglycemia. In specific embodiments, the hypoglycorrhachia is characterized by one or more of cerebrospinal fluid (CSF) glucose of about or less than about 2.2 mmol/L, CSF lactate of about or less than about 1.3 mmol/L, or a ratio of CSF/plasma glucose of about or less than about 0.4.

In some embodiments, the subject is diagnosed with decreased 3-O-methyl-D-glucose uptake in erythrocytes. In certain embodiments, the subject has cerebral fluoro-deoxy-glucose positron emission tomography (PET) findings characterized by diffuse hypometabolism of the cerebral cortex and regional hypometabolism of the cerebellum and thalamus.

In certain embodiments, the odd-chain fatty acid source is administered as a unit dosage of about 2-150 grams. In certain embodiments, the subject is an infant and the odd-chain fatty acid source is administered as a unit dosage of about 1-6 grams/kg. In certain embodiments, the subject is a young child, adolescent, or adult and the odd-chain fatty acid source is administered as a unit dosage of about 0.5-4 grams/kg. In certain embodiments, the odd-chain fatty acid source provides at least about 30-35% of the total calories in the diet of the subject. In certain embodiments, the odd-chain fatty acid source is administered at about 1 to about 10 grams/kg/24 hours, about 1 to about 5 grams/kg/24 hours, or about 1 to about 2 grams/kg/24 hours.

In some embodiments, the odd-chain fatty acid source is administered three times a day, twice a day, or once per day. In certain embodiments, the odd-chain fatty acid source is administered for one month, two months, six months, twelve months, or eighteen months.

In certain embodiments, the odd-chain fatty acid source is administered in the absence of a ketogenic diet. In some embodiments, the odd-chain fatty acid is administered as part of a ketogenic diet.

Some methods comprise oral administration of the odd-chain fatty acid. In particular embodiments, the odd-chain fatty acid is formulated as an oil supplement. In specific embodiments, the odd-chain fatty acid is formulated as a gel capsule.

In certain embodiments, the odd-chain fatty acid is administered in combination with an anti-seizure medication.

In certain embodiments, the odd-chain fatty acid source comprises triheptanoin or a derivative thereof. In specific embodiments, the triheptanoin is ultrapure triheptanoin.

Also included are methods of determining a treatment regimen for a subject with GLUT1 deficiency, as described herein, comprising detecting the level of one or more Krebs cycle intermediates in the subject treated for a GLUT1 deficiency, and determining a treatment regimen based on an increase or decrease in the level of one or more Krebs cycle intermediates.

Also included are methods of monitoring treatment of a subject with GLUT1 deficiency, as described herein, comprising detecting the level of one or more Krebs cycle intermediates or derivatives in the subject treated for a GLUT1 deficiency, wherein an increase or decrease in the level of one or more Krebs cycle intermediates or derivatives compared to a predetermined standard level is predictive of the treatment efficacy of the GLUT1 deficiency treatment.

Also included are methods of determining a treatment regimen for a subject with GLUT1 deficiency, as described herein, comprising detecting the level of one or more ketone bodies in the subject treated for a GLUT1 deficiency and determining a treatment regimen based on an increase or decrease in the level of one or more ketone bodies.

Also included are methods of monitoring treatment of a subject with GLUT1 deficiency, as described herein, comprising detecting the level of one or more ketone bodies in the subject treated for a GLUT1 deficiency, wherein an increase or decrease in the level of one or more ketone bodies compared to a predetermined standard level is predictive of the treatment efficacy of the GLUT1 deficiency treatment. In some embodiments, the ketone bodies are selected from 3-hydroxypentanoate and 3-ketopentanoate.

In certain embodiments, the one or more Krebs cycle intermediates or the one or more ketone bodies are measured in a biological sample from a subject treated for a GLUT1 deficiency. In specific embodiments, the biological sample is selected from blood, skin, hair follicles, saliva, oral mucous, vaginal mucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, brain, and tissue extract sample or biopsy sample.

In some embodiments, the one or more Krebs cycle intermediates or the one or more ketone bodies are measured by brain imaging. In some embodiments, the brain imaging is selected from computed axial tomography, diffuse optical imaging, event-related optical signal, magnetic resonance imaging, functional magnetic resonance imaging, magneto encephalography, positron emission tomography, and single-photon emission computed tomography.

Certain embodiments relate to methods of treating or preventing diseases of the brain affecting energy metabolism in a subject, comprising administering to the subject an effective amount of triheptanoin, where the administration of triheptanoin restores mitochondrial energy function and net biosynthesis through anaplerosis.

Also included are odd-chain fatty acid sources (and related compositions) for use in treating a GLUT1 deficiency and optionally a GLUT1 deficiency-associated condition or disorder. In certain embodiments, the odd-chain fatty acid source provides a clinically-effective or statistically significant therapeutic effect in the treatment of the GLUT1 deficiency and/or the GLUT1 deficiency-associated condition or disorder. In some embodiments, the GLUT1 deficiency-associated condition or disorder is seizures, e.g., epileptic seizures. In specific embodiments, the odd-chain fatty acid source is triheptanoin or a derivative thereof.

DETAILED DESCRIPTION OF THE INVENTION

Embodiments of the present invention relate to the use of anaplerotic therapies to treat brain energy deficiencies such as GLUT1 deficiencies. The anaplerotic therapies described herein include the administration of odd-chain fatty acid sources such as triheptanoin. Odd-chain fatty acid sources supply odd-carbon ketone bodies to the brain (e.g., 3-hydroxypentanoate and 3-ketopentanoate)[12] and replenish substrates of the Krebs cycle, including both acetyl-CoA (to replenish energy production) and propionyl-CoA (to replenish Krebs cycle intermediates and net biosynthesis)[9]. Ketogenic diets, the standard of care for such deficiencies, supply food-derived even-carbon ketones to the brain and thereby replenish acetyl-CoA for energy production, but do not supply the odd-carbon ketones required to replenish propionyl-CoA and net biosynthesis (e.g., for neurotransmitter synthesis). Hence, relative to standard therapies for brain energy deficiencies, odd-chain fatty acid-based anaplerotic therapies provide the advantage of improving both brain energy production and net biosynthesis without the adverse side effects associated with ketogenic diets.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. All publications, patents, and patent applications cited herein are incorporated by reference in their entireties.

The articles "a" and "an" are used herein to refer to one or more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2, or 1% to a reference quantity, level, value, number, frequency, percentage, dimension, size, amount, weight, length, or other unit described herein. In some aspects, the term "about" is used to indicate that a value includes the standard deviation of error for the device or method being employed to determine the value.

The terms "anaplerosis" and "anaplerotic" refer to reactions that form intermediates of one or more metabolic pathways. Examples include reactions that replenish tricarboxylic acid (TCA) cyclic intermediate(s) that have been extracted for biosynthesis, and thereby restore normal energy metabolism. In some aspects, these terms refer to the formation of the TCA cycle intermediates acetyl-CoA and propionyl-CoA/succinyl CoA, for example, by directly or indirectly providing C5-ketone bodies that are converted to acetyl-CoA and propionyl-CoA, the latter being converted to succinyl-CoA. In some instances, heptanoate can also be produced by the liver and delivered to the brain to supply the metabolic needs of glia and neurons (e.g., where the glia convert the heptanoate into other energy intermediates to supply the adjacent neurons). Anaplerotic therapies are based on the existence of an energy deficit in certain tissues in part because of the lack of sufficient TCA cycle intermediates in mitochondria that are otherwise critical for the conversion of food into energy and biosynthetic intermediates. Anaplerotic therapies provide alternative substrates for the TCA cycle to restore its function and thereby enhance ATP production and net biosynthesis in desired tissues, particularly those of the central nervous system.[9,10]

The terms "clinical-efficacy" and "clinically-effective" refer to a treatment that results in a statistically significant therapeutic effect. By "statistically significant" it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

Thus, according to some embodiments, administering an odd-chain fatty acid source according to the methods of the present invention provides a statistically significant therapeutic effect in the treatment of brain energy deficiency such as a GLUT1 deficiency and/or a GLUT1 deficiency-associated condition or disorder (e.g., seizures such as epileptic seizures). In some embodiments, the statistically significant therapeutic effect is determined based on one or more standards or criteria provided by one or more regulatory agencies in the United States, e.g., FDA or other countries. In certain embodiments, the statistically significant therapeutic effect is determined based on results obtained from regulatory agency approved clinical trial set up and/or procedure.

In some embodiments, the statistically significant therapeutic effect is determined based on a patient population of at least 10, 20, 30, 40, 50, 60, 70, 80, 90, 100, 200, 300, 400, 500, 600, 700, 800, 900, 1000 or 2000. In specific embodiments, the statistically significant therapeutic effect is determined based on a patient population that is appropriate for an orphan drug indication. In some embodiments, the statistically significant therapeutic effect is determined based on data obtained from randomized and double-blinded clinical trial set-up. In some embodiments, the statistically significant therapeutic effect is determined based on data with a p-value of less than or equal to about 0.05, 0.04, 0.03, 0.02 or 0.01. In some embodiments, the statistically significant therapeutic effect is determined based on data with a confidence interval greater than or equal to 95%, 96%, 97%, 98% or 99%. In some embodiments, the statistically significant therapeutic effect is determined on approval of Phase III clinical trial of the methods provided by the present invention, e.g., by FDA in the US.

In some embodiments, the clinically-effective or statistically significant therapeutic effect is determined by a randomized double blind clinical trial of a patient population of at least 10, 20, 30, 40, 50, 60, 70, 80, 90, 100, 200, 300 or 350, or a patient population appropriate for an orphan drug indication, treated with an odd-chain fatty acid source optionally in the absence of a ketogenic diet. In some embodiments, the statistically significant therapeutic effect is determined by a randomized clinical trial of a patient population using, for example, occurrence of seizures (e.g., total number of seizures, number of seizures per unit/time), occurrence of dystonic (movements) or other neuurological events described herein, 6-minute walk test, or any combination thereof or any other commonly accepted criteria or endpoints for a GLUT1 deficiency or a GLUT1-associated disorder or condition.

In general, statistical analysis can include any suitable method permitted by a regulatory agency, e.g., FDA in the US or China or any other country. In some embodiments, statistical analysis includes non-stratified analysis, log-rank analysis, e.g., from Kaplan-Meier, Jacobson-Truax, Gulliken-Lord-Novick, Edwards-Nunnally, Hageman-Arrindel and Hierarchical Linear Modeling (HLM) and Cox regression analysis The terms "Krebs cycle," "citric acid cycle (CAC)," and "tricarboxylic acid (TCA) cycle" are used interchangeably to refer to the series of chemical reactions used by aerobic organisms to generate energy through the oxidation of acetate (derived from carbohydrates, fats and proteins) into carbon dioxide and adenosine triphosphate (ATP).

The term "modulating" includes "increasing" or "enhancing," as well as "decreasing" or "reducing," typically in a statistically significant or a physiologically significant amount as compared to a control. An "increased" or "enhanced" amount is typically a "statistically significant" amount, and may include an increase that is about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.3, 4.4, 4.6, 4.8, 5, 6, 7, 8, 9, 10, 15, 20, 30, 40, 50 or more times (e.g., 100, 200, 500, 1000 times) (including all integers and decimal points and ranges in between and above 1, e.g., 5.5, 5.6, 5.7. 5.8, etc.) the amount produced by a control (e.g., the absence or lesser amount of a compound, a different compound or treatment), or the amount of an earlier time-point (e.g., prior to treatment with a compound). A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and decimal points and ranges in between) in the amount or activity produced by a control (e.g., the absence or lesser amount of a compound, a different compound or treatment), or the amount of an earlier time-point (e.g., prior to treatment with a compound).

As used herein, the term "subject" includes a living mammalian organism, such as a human, monkey, cow, sheep, goat, dogs, cat, mouse, rat, guinea pig, or transgenic species thereof. In certain embodiments, the subject is a primate. Non-limiting examples of human subjects or patients include adults, juveniles, infants, and fetuses.

"Substantially" or "essentially" includes nearly totally or completely, for instance, 80%, 85%, 90%, 95%, 96%, 97%, 98%, 99% or greater of some given quantity.

A "therapeutically effective amount" or "effective amount" includes an amount of an agent of the invention which, when administered to a mammal, preferably a human, is sufficient to accomplish a desired or intended result. For example, an "effective amount" of an agent, e.g., triheptanoin, administered to a subject for treatment means that amount which is sufficient to effect an improvement in a GLUT1 deficiency and/or a reduction in one or more of its associated clinical pathologies (e.g., seizures). The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treatment" or "treating" includes (1) inhibiting a disease or condition, such as GLUT1 deficiency and/or its associated conditions, in a subject experiencing or displaying the pathology or symptomatology of the disease or condition (e.g., reducing the pathology or symptomatology reducing, further development of the pathology or symptomatology); (2) ameliorating a disease or condition, such as GLUT1 deficiency and/or its associated conditions, in a subject that is experiencing or displaying the pathology or symptomatology of the disease or condition (e.g., reversing the pathology and/or symptomatology); or (3) effecting any measurable decrease in a disease or condition, such as GLUT1 deficiency and/or its associated conditions, in a subject that is experiencing or displaying the pathology or symptomatology of the disease or condition. For example, triheptanoin and other odd-carbon fatty acid sources can treat symptoms of GLUT1 deficiency in one or more of the following non-limiting ways: increased brain energy levels, increased brain anaplerosis, increased levels of spinal fluid glucose (e.g., such that the cerebrospinal fluid to blood glucose ratio is about 0.50 or above), reduced developmental delay, minimized or reduced cognitive impairment, minimized or reduced occurrence of seizures, or minimized or reduced occurrence of dystonic movements. Also included are reduced developmental abnormalities (such as decreased cognitive function, decreased rate of development and acquisition of new behaviors, difficulty with language or other complex neurologic skills) and reduced movement disorders (e.g., ataxia, chorea, tremors, dysarthria, or myoclonus).

"Prevention" or "preventing" includes: (1) inhibiting the onset of a disease or condition, such as GLUT1 deficiency, in a subject who may be at risk or predisposed to the disease or condition but does not yet experience or display any or all of the pathology or symptomatology of the disease or condition; or (2) slowing or reducing the onset of the pathology or symptomatology of a disease or condition, such as a GLUT1 deficiency, in a subject which may be at risk or predisposed to the disease or condition but does not yet experience or display any or all of the pathology or symptomatology of the disease or condition. Non-limiting examples of symptoms of GLUT1 deficiencies are provided herein.

The term "triheptanoin" refers to a triglyceride of one, two, or three 7-carbon straight chain saturated fatty acids. Triheptanoin is considered an anaplerotic compound. The term "tripentanoin" refers to a triglyceride of one, two, or three 5-carbon straight-chain saturated fatty acids. Odd-carbon fatty acid sources including triheptanoin and tripentanoin can work similarly in allowing both the production of acetyl-CoA to supply the TCA cycle and also the propionyl-CoA that gets converted to succinyl-CoA in the anaplerotic process. Other examples odd-chain fatty acid sources (e.g., triglycerides, diglycerides, free fatty acids) are described herein.

Methods of Treatment

Embodiments of the present invention relate to methods of treating brain energy deficiencies (i.e., diseases of the brain affecting energy metabolism) in a subject in need thereof, comprising administering to the subject an odd-chain fatty acid source. Such brain energy deficiencies typically lead to brain dysfunction because of the inadequate production of energy and net biosynthesis intermediates required by glial cells and neurons. Ideally, the odd-chain fatty acid source restores mitochondrial function through anaplerosis, for example, by increasing the availability of acetyl-CoA and propionyl-CoA/succinyl-CoA in central nervous system tissues such as glial cells and neurons. Examples of brain energy deficiencies include but are not limited to GLUT1 deficiencies, epilepsy, epilepsy-like disorders, seizure disorders, ictal disorders, postictal disorders, interictal disorders, and paroxysmal brain dysfunctions.

In particular embodiments, the disease is a Glucose transporter 1 (GLUT1) deficiency or a symptom or condition associated with a GLUT1 deficiency. GLUT1 deficiencies include, for example, De Vivo disease, GLUT1 deficiency syndrome (GLUT1DS or G1D), and glucose transporter protein syndrome (GTPS). GLUT1 facilitates the transport of glucose across the plasma membrane of mammalian cells. It is also referred to as solute carrier family 2-facilitated glucose transporter member 1 (SLC2A1). GLUT1 deficiencies are typically caused by mutations or other defects in the GLUT1 gene, which result in decreased glucose transport across the blood-brain barrier. In certain instances, the subject has or has been diagnosed as having one or more disease-associated mutations in the GLUT1 gene (the SLC2A1 gene). Most patients carry heterozygous de novo mutations in the GLUT1-gene but autosomal dominant and recessive transmission have also been identified (see Verrotti et al., Eur J. Paedeatr. Neurol. 16:3-9, 2012).

GLUT1 and related deficiencies can be characterized, for example, by hypoglycorrhachia optionally without hypoglycemia. In some instances, hypoglycorrhachia is characterized by low cerebrospinal fluid (CSF) glucose, (<2.2 mmol/L), low CSF lactate, and/or a lowered CSF/plasma glucose ratio (<0.4). This decrease in glucose transport/levels leads to brain energy deficiencies in which the glia are unable to use glucose or to supply lactate to neurons. Accordingly, in certain aspects, the subject has a low level of glucose in CSF, low levels of lactate in CSF, and/or a lowered CSF/plasma glucose ratio. For instance, in some aspects the subject has CSF glucose of about or less than about 2.2, 2.1, 2.0, 1.9, 1.8, 1.7, 1.6, 1.5, 1.4, 1.3, 1.2, 1.1, 1.0, 0.9, 0.8, 0.7, 0.6, or 0.5 mmol/L (e.g., prior to effective treatment). In some aspects the subject has CSF lactate of about or less than about 1.3, 1.2 1.1, 1.0, 0.9, 0.8, 0.7, 0.6, or 0.5 mmol/L (e.g., prior to effective treatment). In certain aspects the subject has a ratio of CSF/plasma glucose of about or less than about 0.4, 0.35, 0.3, 0.25, 0.2, 0.15, or 0.1 (e.g., prior to effective treatment).

In some instances, the subject is diagnosed with decreased 3-O-methyl-D-glucose uptake in erythrocytes. Optionally, the subject has cerebral fluoro-deoxy-glucose positron emission tomography (PET) findings characterized by diffuse hypometabolism of the cerebral cortex and regional hypometabolism of the cerebellum and thalamus.

GLUT1 deficiencies associate with conditions such as inadequate brain function, seizures, motor disturbances, cognitive impairment, developmental delay, acquired microcephaly, spasticity, ataxia, paroxysmal exertion-induced dyskinesia, and other clinical manifestations. Thus, in certain embodiments the subject has a GLUT1 deficiency and a GLUT1 deficiency-associated condition or disorder, and the methods comprise treating the GLUT1 deficiency, the GLUT1 deficiency-associated condition/disorder, or both. In specific embodiments, the GLUT1 deficiency-associated condition/disorder includes seizures and the subject has had or is at risk for having seizures. Seizures are episodes of disturbed brain function that cause changes in attention or behavior. They are caused by abnormally excited electrical signals in the brain. In particular embodiments, the subject has had or is at risk for having epileptic seizures. By "epilepsy" (also called epileptic seizure disorder) is meant is a chronic brain disorder characterized by recurrent, unprovoked seizures. The seizures are caused by sudden, usually brief, excessive electrical discharges in neurons. Epileptic attacks can lead to loss of awareness, loss of consciousness and/or disturbances of movement, autonomic function, sensation (including vision, hearing and taste), mood and/or mental function. Types of seizures include simple partial, complex partial and generalized seizures, such as tonic, clonic, tonic-clonic, absence, Status epilepticus, atonic and myoclonic seizures. The methods of the present invention are particularly suited to treatment of medically-refractory epilepsy, chronic epilepsy, acute epilepsy or drug resistant epilepsy. In particular embodiments, the subject has had about or at least about 1, 2, 3, 4, 5, 6, 7, 8, 9, or 10 or more prior seizures, e.g., epileptic seizures. In certain embodiments, administration of the odd-chain fatty acid source reduces the frequency or occurrence of seizures in the subject by about or at least about 10, 20, 30, 40, 50, 60, 70, 80, 90, 100% over a defined period of time, for instance, over 1, 2, 3, 4, 5, 6, 7, 8 weeks or more, over 1, 2, 3, 4, 5, 6, 7, 8, 9, 10, 11, 12 months or more, or over 1, 2, 3, 4, 5, 6, 7, 8, 9, 10 years or more.

Anaplerotic therapy using odd-chain fatty acid sources such as odd-chain triglycerides (e.g., triheptanoin, a 7-carbon triglyceride) can be used to replenish one or more substrates of the TCA cycle and thereby correct the energy and net biosynthesis deficits in a GLUT1 deficiency. In some aspects, anaplerotic therapy halts or reverses the disease progression and clinical neurological symptoms in patients with GLUT1 deficiency.

The terms "odd-chain" fatty acids and "odd-carbon" fatty acids are used interchangeably to refer to fatty acids (carboxylic acids with an aliphatic tail) that consist of an odd number of carbon atoms. The fatty acids can be saturated or unsaturated. Examples of odd-chain fatty acids include propionic acid, pentanoic acid, heptanoic acid, nonanoic acid and undecanoic acid. An odd-chain fatty acid "source" refers to a molecule or composition that comprises at least one odd-chain fatty acid. Examples include odd-chain free fatty acids, triglycerides containing at least one odd-chain fatty acid, diglycerides containing at least one odd-chain fatty acid, monoglycerides containing an odd-chain fatty acid, and phospholipids containing at least one odd-chain fatty acid, including combinations/mixtures thereof. Also included are derivatives of any of the odd-chain fatty acid-containing molecules described herein.

As noted above, particular examples of odd-chain fatty acid sources include odd-chain fatty acid triglycerides (e.g., triheptanoin, tripentanoin), odd-chain fatty acid diglycerides, and odd-chain fatty acid monoglycerides. Thus, in some embodiments, the treatment of a GLUT1 deficiency comprises administration of an effective amount of a triglyceride that comprises at least one odd-chain fatty acid, at least two odd-chain fatty acids, or three odd-chain fatty acids. In some embodiments, the treatment of a GLUT1 deficiency comprises administration of an effective amount of a diglyceride that comprises at least one odd-chain fatty acid or at least two odd-chain fatty acids. In some embodiments, the treatment of a GLUT1 deficiency comprises administration of an effective amount of a monoglyceride that comprises an odd-chain fatty acid. The odd-chain triglyceride or diglyceride or monoglyceride can contain short, medium, and/or long odd-chain fatty-acids.

In some embodiments, the odd-chain triglyceride includes 5-carbon triglycerides, 7-carbon triglycerides, 9-carbon triglycerides, and/or 15-carbon triglycerides. In certain embodiments, the odd-chain diglyceride includes 5-carbon diglycerides, 7-carbon diglycerides, 9-carbon diglycerides, and/or 15-carbon diglycerides. In particular embodiments, the odd-chain monoglyceride includes 5-carbon monoglycerides, 7-carbon monoglycerides, 9-carbon triglycerides, and/or 15-carbon monoglycerides. Some methods employ triglycerides, diglycerides, and/or monoglycerides of C5 fatty acids, triglycerides of C7 fatty acids, and/or triglycerides of C9 fatty acids. Combinations of triglycerides, diglycerides, and/or monoglycerides can also be employed. Specific examples include mixtures of 7-carbon triglycerides and 5-carbon triglycerides. Also included are derivatives of the odd-chain triglycerides described herein.

In certain embodiments, the odd-chain fatty acid source comprises or consists of triheptanoin (glyceryl triheptanoate) or tripentanoin. Also included are salts, prodrugs, analogues, derivatives, substituted, unsaturated, branched forms, and derivatives thereof. Triheptanoin is a triglyceride made by the esterification of three n-heptanoic acid molecules and glycerol and can be obtained by the esterification of heptanoic acid and glycerol by any means known in the art. Triheptanoin is also commercially available through Sasol (Witten, Germany) as Special Oil 107, although without limitation thereto. Heptanoic acid is found in various fusel oils in appreciable amounts and can be extracted by any means known in the art. It can also be synthesized by oxidation of heptaldehyde with potassium permanganate in dilute sulfuric, acid. Heptanoic acid is also commercially available through Sigma Chemical Co. (St. Louis, Mo.). In some embodiments, the triheptanoin is ultrapure triheptanoin, as described in U.S. provisional application 61/709, 080 (incorporated by reference in its entirety). There are no toxic side effects reported with the long-term use of triheptanoin in humans.

Triheptanoin is metabolized in the liver to generate C5-ketone bodies and heptanoate as sources of energy for the brain but without the need to induce generalized ketosis (e.g., via a strict diet), and thus exhibits significantly greater safety than other methods of treating GLUT1 deficiencies. In addition, since ketone body formation is supplied from medium chain fatty acids that do not suppress ketone body formation in the liver, the use of triheptanoin only requires approximately 25-35% fat calories from triheptanoin which can include carbohydrates, rather than the 70-90% calories from fat devoid of carbohydrates required for a traditional ketogenic diet.

After enteral absorption of triheptanoin, most of the heptanoate reaching the liver is β-oxidized into 1× anaplerotic propionyl-CoA and 2× acetyl-CoA.[9] The excess acetyl-CoA and propionyl-CoA are channeled to produce C4- and C5-ketone bodies, which are exported from the liver to peripheral tissues.[9,10] The production of these ketone bodies from dietary triheptanoin occurs even when a meal contains carbohydrates. This results because the oxidation of heptanoate (a medium chain fatty acid) in liver mitochondria is not regulated by the carnitine palmitoyltransferase system, the activity of which is otherwise inhibited by dietary carbohydrates.[9] However, to optimize its anaplerotic effects, triheptanoin should represent at least 30 to 35% of the total calories.[11] Otherwise, glucose would be the main source of energy supply and the oxidation of triheptanoin could be reduced. The C5-ketone bodies (3-hydroxypentanoate and 3-ketopentanoate) cross the blood-brain barrier and generate anaplerotic propionyl- and acetyl-CoA for the Krebs cycle in brain tissues.[12] In addition to the C5-ketone bodies, the release of heptanoate occurs after administration (e.g., ingestion) of triheptanoin. Heptanoate can cross the blood brain barrier and be metabolized in the glia to generate energy metabolites for the neurons. Given its odd-chain length, it can also create anaplerotic intermediates and restore TCA cycle function in the brain.

In some embodiments, the odd-chain fatty acid source is administered instead of or in the absence of a ketogenic diet (or a substantially ketogenic diet). That is, in some instances, the subject is not on a ketogenic diet or as has failed to follow a ketogenic diet. Failure to follow a ketogenic diet can include instances where the subject is unable to maintain the strict food choices or is medically unable to stay on a ketogenic diet because of side effects or issues with other medications and/or disorders. By "absence of a ketogenic diet" is meant a dietary intake which does not have a higher than normal fat content compared to carbohydrate and protein. In some embodiments, an "absence of a ketogenic diet" is a diet is which the ratio by weight of fat to combined protein and carbohydrate is less than 3:1, and may be 2:1, 1:1, 0.5:1 or a ratio where the fat content is even lower, or where fat is absent.

In any of the treatment methods described herein, the combination of C5-ketone bodies, heptanoate, and/or the intermediary metabolism of the brain in glia or neurons may be involved in replacing the energy deficiency state that leads to defects in brain energy metabolism, including GLUT1-deficiency and its associated symptoms/pathologies.

Certain embodiments therefore include the use of odd-chain fatty acid sources (e.g., triheptanoin and related compositions) as dietery supplements or neutraceuticals, for example, to improve or support brain energy, improve or support brain metabolism, improve or support improve brain function, or improve or support nervous system (e.g., CNS) energy, metabolism or function.

Administration and Dosages

Administration of the odd-chain fatty acid sources in pure form or in an appropriate pharmaceutical composition can be carried out via any of the accepted modes of administration of agents for serving similar utilities. Typical routes of administering an odd-chain fatty acid source or a composition comprising the same include, without limitation, oral, topical, transdermal, inhalation, parenteral, sublingual, buccal, rectal, vaginal, and intranasal routes. The term parenteral as used herein includes subcutaneous injections, intravenous, intramuscular, intrasternal injection or infusion techniques. In specific embodiments, the odd-chain fatty acid source is administered or ingested orally.

An odd-chain fatty acid source or related composition may be in the form of a solid or liquid. In one aspect, the carrier(s) are particulate, so that the compositions are, for example, in tablet or powder form. The carrier(s) may be liquid, with the compositions being, for example, an oral oil, an oral syrup, or an injectable liquid. In specific embodiments, the composition is a oil supplement of triheptanoin or a derivative thereof.

When intended for oral administration, the pharmaceutical composition is preferably in either solid (e.g., powder) or liquid form, where semi-solid, semi-liquid, suspension, and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an oil, elixir, syrup, solution, emulsion, or suspension. The liquid may be for oral administration or for delivery by injection. When intended for oral administration, a composition may contain, in addition to the odd-chain fatty acid(s), one or more of sweetening agents, preservatives, dye/colorants and flavor enhancers. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

Certain compositions may be intended for rectal administration, in the form, for example, of a suppository, which will melt in the rectum and release the odd-chain fatty acid source. The composition for rectal administration may contain an oleaginous base as a suitable non-irritating excipient. Such bases include, without limitation, lanolin, cocoa butter and polyethylene glycol.

Odd-chain fatty acid sources and related compositions are formulated so as to allow the active ingredients contained therein to be bioavailable upon administration of the composition to a subject. Compositions that will be administered to a subject or patient usually take the form of one or more dosage units, where for example, a tablet or capsule (e.g., gel capsule) may be a single dosage unit, and a container may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). In certain aspects, the composition to be administered contains a therapeutically effective amount of an odd-chain fatty acid source, for treatment of a disease or condition of interest.

In some embodiments, a unit dosage comprises about or at least about 2 g to about 150 g, or about 2 g, 3 g, 4 g, 5 g, 10 g, 15 g, 20 g, 25 g, 30 g, 35 g, 40 g, 45 g, 50 g, 55 g, 60 g, 65 g, 70 g, 75 g, 80 g, 90 g, 95 g, 100 g, 125 g or 150 g, or more of an odd-chain fatty acid source (e.g., triheptanoin).

The frequency of administration of the compositions described herein may vary from once-a-day (QD) to twice-a-day (BID) or thrice-a-day (TID), etc., the precise frequency of administration varying with, for example, the patient's condition, the dosage etc Table 1 below provides energy conversion values useful for calculating dosages suitable for methods provided herein. Additional information can also be found in Gidding et al. (Dietary Recommendations for Children and Adolescents: A Guide for Practitioners, Pediatrics, 117:544-559 (2006); incorporated herein by reference in its entirety).

TABLE 1

Energy Conversion Values
Table 1: Energy Conversion Values

| Energy Density | kJ/g | kCal/g |
| --- | --- | --- |
| Fat | 37 | 9 |
| Ethanol (drinking alcohol) | 29 | 7 |
| Proteins | 17 | 4 |
| Carbohydrates | 17 | 4 |
| Organic acids | 13 | 3 |
| Polyols (sugar alcohols, sweeteners) | 10 | 2.4 |
| Fiber | 8 | 2 |

In certain embodiments a dosage is calculated by the weight of the subject. According to the World Health Organization (WHO), boys from birth to 5 years of age range in mass from approximately 2 kg to 30 kg. Boys of 5 years to 10 years of age range in mass from approximately 10 kg to 50 kg. Girls from birth to 5 years of age range in mass from approximately 2 kg to 30 kg. Girls of 5 years to 10 years of age range in mass from approximately 10 kg to 52 kg. See, for example, the WHO Growth Standards, hereby incorporated by reference.

In certain embodiments, the dosage of the odd-chain fatty acid source, e.g., C7 carbon source such as triheptanoin, is from about 2-4 grams/kg for infants, 1-2 grams/kg for young children (e.g., prepubescent or pubescent), or about 1 gram/kg for adolescents (e.g., post-pubescent) and adults. In specific embodiments, the dosage ranges from about 1-6, 1-2, 2-3, 3-4, 4-5, or 5-6 grams/kg for infants, 0.5-4, 0.5-1, 1-1.5, 1.5-2, 2-2.5, 2.5-3, 3-3.5, or 3.5-4 grams/kg for young children, or about 0.5-4, 0.5-1, 1-1.5, 1.5-2, 2-2.5, 2.5-3, 3-3.5, or 3.5-4 grams/kg for adolescents and adults.

In some embodiments, the unit dosage is the desired daily dosage (e.g., grams/kg) multiplied by the average weight of the subject group, and optionally divided by times per day for administration. For example, in some embodiments, the unit dosage for infants is 2-4 grams/kg multiplied by an average infant's weight, and optionally divided by one, two, three, four, five or six for daily administration. In particular embodiments, the unit dosage for young children through school age is 1-2 grams/kg multiplied by an average young child's weight, and optionally divided by one, two, three, four, five or six for daily administrations. In some embodiments, the unit dosage for adolescents and adults is about 1 grams/kg multiplied by an average adolescent's or adult's weight, and optionally divided by one, two, three, or four for daily administration. In some embodiments the unit dosage volume is in milliliters or liters.

In some embodiments, the odd-chain fatty acid source (e.g., triheptanoin) is provided in solution and/or oil from between about 0.25 g/mL (i.e., 0.25 g per cc) to about 2 g/mL (i.e., 0.25 g per cc). In certain embodiments, the odd-chain fatty acid source (e.g., triheptanoin) is provided (e.g., in solution and/or oil) at about 0.25 g/mL, 0.5 g/mL, 0.75 g/mL, 1 g/mL, 1.25 g/mL, 1.5 g/mL, 1.75 g/ml or 2 g/mL.

In some embodiments, the odd-chain fatty acid source (e.g., triheptanoin) is administered at about 1 to about 10 grams/kg/24 hours, about 1 to about 5 grams/kg/24 hours or about 1 to about 2 grams/kg/24 hours. In some embodiments, the odd-chain fatty acid source (e.g., triheptanoin) is administered at about 2-4 grams/kg/24 hours for infants. In some embodiments, the odd-chain fatty acid source (e.g., triheptanoin) is administered at about 2, 3 or 4 grams/kg/24 hours for infants. In certain embodiments, the odd-chain fatty acid source (e.g., triheptanoin) is administered at about 1-2 grams/kg/24 hours for children through school age. In some embodiments, the odd-chain fatty acid source (e.g., triheptanoin) is administered at about 1 or 2 grams/kg/24 hours for children through school age. In some embodiments the odd-chain fatty acid source (e.g., triheptanoin) is administered at about 1 gram/kg/24 hours for adolescents and adults.

Based on the suitable dosage, the odd-chain fatty acid source (e.g., triheptanoin) can be provided in various suitable unit dosages. For example, an odd-chain fatty acid source can comprise a unit dosage for administration one or multiple times per day, for 1-7 days per week. Such unit dosages can be provided as a set for daily, weekly and/or monthly administration.

In some embodiments, the odd-chain fatty acid source (e.g., triheptanoin) is administered about six times a day, about five times a day, about four times a day, about three times a day, about twice a day, or about once per day.

In certain embodiments, the daily dosage is divided into 1 to 6 daily dosages, 1 to 5 daily dosages, or 1 to 4 daily dosages. In some embodiments, the daily dosage is divided into 1 to 4 daily doses, 1 to 5 daily doses, or 1 to 6 daily doses of 2, 5, 10, 15, 20, 25, 30, 35, 40 or 50 cc. In some embodiments, the daily dosage is divided into 4 daily doses of 15 cc to 20 cc for an adult. In specific embodiments, the odd-chain fatty acid source (e.g., triheptanoin) is provided in 1 g/mL and the daily dosage of 1 g/kg/day is divided into 4 daily dosages.

In some embodiments, the odd-chain fatty acid source (e.g., triheptanoin) is administered for one week, two weeks, one month, two months, six months, twelve months or eighteen months.

In some embodiments, the odd-chain fatty acid source (e.g., triheptanoin) is administered as part of a dosing regimen so as to maintain a constant level of the odd-chain fatty acid source in the subject. In some embodiments, the odd-chain fatty acid source can be administered multiple times per day so as to maintain a constant level in the blood.

In some embodiments, the dosage of the odd-chain fatty acid source (e.g., triheptanoin) provides at least about 10% to about 50%, at least about 20% to about 40%, at least about 25% to about 35%, or at least about 30% to about 35% of the total calories in the diet of said subject. In some embodiments, the odd-chain fatty acid source provides at least about 25-35% of the calories in the diet of infants and/or young children.

Odd-chain fatty acid sources may also be administered simultaneously with, prior to, or after administration of one or more other therapeutic or biologically active agents, dietary supplements, or any combination thereof. Such combination therapies include administration of a single pharmaceutical dosage formulation which contains an odd-chain fatty acid source and one or more additional active agents, as well as administration of the odd-chain fatty acid source and each active agent in its own separate pharmaceutical dosage formulation. For example, an odd-chain fatty acid source and the other active agent can be administered to the patient together in a single oral dosage formulation such as a tablet, capsule (e.g., gel capsule), syrup, or oil, or each agent administered in separate oral dosage formulations. Where separate dosage formulations are used, the odd-chain fatty acid source and one or more additional active agents can be administered at essentially the same time, i.e., concurrently, or at separately staggered times, i.e., sequentially. Combination therapy is understood to include all these regimens.

In some embodiments, the odd-chain fatty acid source (e.g., triheptanoin) is administered in combination with a ketogenic diet, a partial ketogenic diet, or a C4 ketogenic diet. By "ketogenic diet" is meant a high fat and low carbohydrate and protein diet. Typically, a ketogenic diet contains a 3:1 to 4:1 ratio by weight of fat to combined protein and carbohydrate. A ketogenic diet may refer to a classical ketogenic diet comprising predominantly natural fats (inclusive of normal dietary fats and suitably long-chain triglycerides) or a ketogenic diet comprising predominantly medium chain triglycerides and suitably, even medium chain triglycerides. By "C4 ketogenic diet" is meant a high fat and low carbohydrate and protein diet. Typically, a C4 ketogenic diet contains a 3:1 to 4:1 ratio by weight of even chain fat to combined protein and carbohydrate. A C4 ketogenic diet increases the C4 ketones, β-hydroxybutyrate and acetoacetate, but not C5 ketones. A C4 ketogenic diet may refer to a classical ketogenic diet comprising predominantly natural fats (inclusive of normal dietary fats and suitably long-chain triglycerides) or a ketogenic diet comprising predominantly medium chain triglycerides and suitably, even medium chain triglycerides, mostly C8 and C10 oil(s). In these and related embodiments, the odd-chain fatty acid source can be substituted for about 5%, 10%, 15%, 20%, 25%, 30%, 35%, 40%, 45%, 50%, 55%, 60%, 65%, 70%, 75%, 80%, 85%, 90% or 95% of the calories or amount of the fat portion of the full or partial ketogenic diet.

In some embodiments, the odd-chain fatty acid source (e.g., triheptanoin) is combined with or administered in combination with a food entity. Food entities include for example yogurt, sauces, shakes, or any other food with which the odd-chain fatty acid source can be combined. In some embodiments, the odd-chain fatty acid source is combined with an emulsifying component. In some embodiments, the food component comprises an emulsifying component.

In some embodiments, odd-chain fatty acid source (e.g., triheptanoin) is administered in combination with an anti-seizure drug. Also included are pharmaceutical compositions that comprise an odd-chain fatty acid source and an anti-seizure drug. Examples of anti-seizure drugs include but are not limited to Acetazolamide, Banzel, Barbexaclone, Beclamide, Brivaracetam, Carbamate, carbamazepine (Tegretol), Carbatrol, Carboxamide, Cerebyx, Clobazam, clonazepam (Klonopin), Clorazepate, Depakene, Depakote, Depakote ER, Depakote Sprinkles, Diamox, Diamox Sequels, Diastat, Diazepam, Dilantin, Epitol, Eslicarbazepine acetate, Ethadione, Ethosuximide, Ethotoin, Ezogabine, Felbamate, Felbatol, Fosphenytoin, Frisium, Fycompa, gabapentin (Neurontin), Gabitril, Inovelon, Keppra, Keppra XR, Klonopin, lacosamide (Vimpat), Lamictal, lamotrigine (Lamictal), lamotrigine (Lamictal), lamotrigine (Lamictal), levetiracetam (Keppra), Lorazepam, Luminal, Lyrica, M phenytoin, Mesuximide, Methazolamide, Methylphenobarbital, Midazolam, Mysoline, Neurontin, nimetazepam, Onfi, Oxcarbazepine, oxcarbazepine (Trileptal), Paraldehyde, Paramethadione, Perampanel, Phenacemide, Pheneturide, Phenobarbital, Phensuximide, Phenytek, phenytoin (Dilantin), Phenytoin Sodium, Potassium bromide, Potiga, pregabalin (Lyrica), Primidone, rufinamide (Banzel), Sabril, Seletracetam, Stiripentol, Sultiame, Tegretol, Tegretol XR, temazepam, Tiagabine, topiramate (Topamax), Trileptal, Trileptal, Trileptal, Trimethadione, Trimethadione, Trimethadione, valproic acid (Depakote), Valpromide, Valnoctamide, vigabatrin (Sabril), vigabatrin (Sabril), Vimpat, Zarontin, or zonisamide (Zonegran). In certain of these and related embodiments, the subject has a GLUT1 deficiency and is at risk for having seizures, or has had at least 1, 2, 3, 4, 5, 6, 7, 8, 9, or 10 or more prior seizures. In certain embodiments, administration of the odd-chain fatty acid source in combination with the anti-seizure drug reduces the frequency or occurrence of seizures in the subject by about or at least about 10, 20, 30, 40, 50, 60, 70, 80, 90, 100% over a defined period of time, for instance, over 1, 2, 3, 4, 5, 6, 7, 8 weeks or more, over 1, 2, 3, 4, 5, 6, 7, 8, 9, 10, 11, 12 months or more, or over 1, 2, 3, 4, 5, 6, 7, 8, 9, 10 years or more.

Monitoring Treatment

Certain embodiments include methods for monitoring and/or predicting the treatment efficacy of a GLUT1 deficiency treatment as described herein. Such methods include detecting the level of one or more Krebs cycle intermediates or their derivatives in a subject (or in a biological sample from the subject) treated for a GLUT1 deficiency, wherein an increase or decrease in the level of one or more Krebs cycle intermediates or their derivatives compared to a predetermined standard level indicates or is predictive of the treatment efficacy of the GLUT1 deficiency treatment.

Also included are methods for determining the treatment regimen for treating a GLUT1 deficiency as described herein. Such methods include detecting the level of one or more Krebs cycle intermediates or their derivatives in a subject (or in a biological sample from the subject) treated for a GLUT1 deficiency and determining a treatment regimen based on an increase or decrease in the level of the one or more Krebs cycle intermediates.

Examples of Krebs cycle intermediates include acetyl-CoA, propionyl-CoA, and succinyl-CoA, including precursors and derivatives thereof.

Some embodiments include methods for monitoring and/or predicting the treatment efficacy of a GLUT1 deficiency treatment as described herein, comprising detecting the level of one or more ketone bodies in subject (or in a biological sample from the subject) treated for a GLUT1 deficiency, wherein an increase or decrease in the level of one or more ketone bodies compared to a predetermined standard level indicates or is predictive of the treatment efficacy of the GLUT1 deficiency treatment.

Also included are methods for determining the treatment regimen for treating a GLUT1 deficiency as described herein. Such methods include detecting the level of one or more ketone bodies in a subject (or in a biological sample from the subject) treated for a GLUT1 deficiency and determining a treatment regimen based on an increase or decrease in the level of one or more ketone bodies.

Examples of ketone bodies include but are not limited to beta-hydroxypentanoic acid (BHP), beta-ketopentanoic acid (BKP), 3-hydroxypentanoate, and 3-ketopentanoate.

The levels of one or more Krebs cycle intermediates or their derivatives or one or more ketone bodies can be measured or determined using any of a variety of methods known to those of skill in the art.

For example, in some embodiments, the one or more Krebs cycle intermediates and/or ketone bodies or their derivatives are measured in a biological sample (obtained) from a subject treated for a GLUT1 deficiency. In some embodiments, the biological sample is selected from blood, skin, hair follicles, saliva, oral mucous, vaginal mucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, brain, and tissue extract sample or biopsy sample. In specific embodiments, C5 levels are measured in the blood and/or urine.

In some embodiments, the one or more Krebs cycle intermediates and/or ketone bodies or their derivatives are measured in the brain of the subject. For example, in some embodiments, the one or more Krebs cycle intermediates and/or ketone bodies or their derivatives are measured by brain imaging. In some embodiments, the brain imaging includes but is not limited to computed axial tomography, diffuse optical imaging, event-related optical signal, magnetic resonance imaging, NMR spectroscopy, functional magnetic resonance imaging, magneto encephalography, positron emission tomography, electroencephalography, near infrared spectroscopy, and single-photon emission computed tomography.

Additionally, the levels of the one or more Krebs cycle intermediates and/or ketone bodies or their derivatives can be determined in order to generate a composite of the level of the Krebs cycle intermediates and/or ketone bodies. Certain methods include determining a composite level of a panel of selected Krebs cycle intermediates and/or ketone bodies. The composite can include but is not limited to any of the Krebs cycle intermediates or ketone bodies described herein. In specific embodiments, C5 ketone body level information is included as part of the composite.

REFERENCES

1. Seidner G, Alvarez M G, Yeh J I, et al. GLUT-1 deficiency syndrome caused by haploinsufficiency of the blood-brain barrier hexose carrier. Nat Genet 1998; 18:188-91.
2. Striano P, Weber Y G, Toliat M R, et al. GLUT1 mutations are a rare cause of familial idiopathic generalized epilepsy. Neurology 2012; 78:557-62.
3. Wang D, Pascual J M, Yang H, et al. Glut-1 deficiency syndrome: clinical, genetic, and therapeutic aspects. Ann Neurol 2005; 57:111-8.
4. Brockmann K. The expanding phenotype of GLUT1-deficiency syndrome. Brain Dev 2009; 31:545-52.
5. Schneider S A, Paisan-Ruiz C, Garcia-Gorostiaga I, et al. GLUT1 gene mutations cause sporadic paroxysmal exercise-induced dyskinesias. Mov Disord 2009; 24:1684-8.
6. Graham J M, Jr. GLUT1 deficiency syndrome as a cause of encephalopathy that includes cognitive disability, treatment-resistant infantile epilepsy and a complex movement disorder. Eur J Med Genet 2011.
7. Klepper J, Leiendecker B. GLUT1 deficiency syndrome—2007 update. Dev Med Child Neurol 2007; 49:707-16.
8. Freeman J M, Kossoff E H. Ketosis and the ketogenic diet, 2010: advances in treating epilepsy and other disorders. Adv Pediatr 2010; 57:315-29.
9. Brunengraber H, Roe C R. Anaplerotic molecules: current and future. J Inherit Metab Dis 2006; 29:327-31.
10. Roe C R, Mochel F. Anaplerotic diet therapy in inherited metabolic disease: therapeutic potential. J Inherit Metab Dis 2006; 29:332-40.
11. Roe C R, Sweetman L, Roe D S, David F, Brunengraber H. Treatment of cardiomyopathy and rhabdomyolysis in long-chain fat oxidation disorders using an anaplerotic odd-chain triglyceride. J Clin Invest 2002; 110:259-69.
12. Mochel F, DeLonlay P, Touati G, et al. Pyruvate carboxylase deficiency: clinical and biochemical response to anaplerotic diet therapy. Mol Genet Metab 2005; 84:305-12.
13. Roe C R, Yang B Z, Brunengraber H, Roe D S, Wallace M, Garritson B K. Carnitine palmitoyltransferase II deficiency: successful anaplerotic diet therapy. Neurology 2008; 71:260-4.
14. Mochel F et al. Dietary anaplerotic therapy improves peripheral tissue energy metabolism in patients with Huntington's disease. Eur J Hum Genet 2010; 18:1057-60.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of non-critical parameters that could be changed or modified to yield essentially similar results.

EXAMPLES

Example 1

Subjects exhibiting GLUT1 deficiency and associated clinical symptoms are treated with triheptanoin. Subjects are administered triheptanoin with each meal at a dosage sufficient to account for about 30-35% of the subject's caloric intake with or without other anti-epileptic drugs. The subjects' seizure frequency is reduced and their neurologic and movement disorder is improved due to the restoration of brain energy metabolism and net biosynthesis.

The invention claimed is:

1. A method of treating a movement disorder associated with GLUT1 deficiency in a human subject in need thereof, the method comprising administering to the human subject an effective amount of triheptanoin, wherein the movement disorder is selected from dystonic movements, ataxia, chorea, tremors, dysarthria, and myoclonus.

2. The method of claim 1, wherein triheptanoin is administered once per day, twice per day, three times per day, or four times per day.

3. The method of claim 1, wherein triheptanoin is administered for one week, two weeks, one month, two months, six months, twelve months, or eighteen months.

4. The method of claim 1, wherein triheptanoin is administered in an amount which provides about 20% to about 40% of the total calories in the diet of said subject.

5. The method of claim 1, wherein triheptanoin is administered in an amount which provides about 30% to about 35% of the total calories in the diet of said subject.

6. The method of claim 1, wherein triheptanoin is administered in an amount about 1 gram/kg/24 hours to about 10 grams/kg/24 hours.

7. The method of claim 1, wherein triheptanoin is administered at about 1 gram/kg/24 hours to about 5 grams/kg/24 hours.

8. The method of claim 1, wherein triheptanoin is administered at about 1 gram/kg/24 hours to about 2 grams/kg/24 hours.

* * * * *